US00PP09371P

United States Patent [19]

Zerr

[11] Patent Number: Plant 9,371

[45] Date of Patent: Nov. 14, 1995

[54] POINSETTIA PLANT NAMED FISPIC

[75] Inventor: Katharina Zerr, Simmern, Germany

[73] Assignee: Florfis AG, Binningen, Switzerland

[21] Appl. No.: 328,051

[22] Filed: Oct. 24, 1994

[30] Foreign Application Priority Data

Dec. 29, 1993 [DE] Germany ..... EUP 147

[51] Int. Cl.[6] ..... A01H 5/00

[52] U.S. Cl. ..... Plt./86.4

[58] Field of Search ..... Plt./86.4

[56] References Cited

U.S. PATENT DOCUMENTS

P.P. 5,492 6/1985 Gutbier ..... Plt./86.4

P.P. 8,259 6/1993 Jacobsen ..... Plt./86.4

*Primary Examiner*—James R. Feyrer

*Attorney, Agent, or Firm*—Foley & Lardner

[57] ABSTRACT

A distinct cultivar of Poinsettia plant named Fispic, characterized by the combined traits of dark orange-red bract color, low and compact plant habit, medium green foliage, comparatively narrow and somewhat pointed bracts, and no heat delay and no tendency to develop a bluish tint, thereby making the new cultivar well suited for early culture under high temperatures.

1 Drawing Sheet

Fispic is a product of a mutation induction program carried out by the inventor in Hillscheid, Germany in 1991. The primary objective of the induction program was to expand the bract color ranges of Peterstar, disclosed in U.S. Plant Pat. No. 8,259 characterized by its bright red bract color, medium green foliage, comparatively compact plant habit, medium early response in autumn, and good branching ability.

The irradiation program resulting in the new cultivar comprised expressing rooted cuttings of the parent cultivar to an X-ray source of 30 Gy in Ahrensburg, Germany under the supervision of the inventor Katharina Zerr in 1991. The irradiated plants were grown out in a greenhouse in Hillscheid, Germany and were asexually propagated by taking cuttings. These cuttings were grown outdoors near Galdar, Gran Canaria, Spain, under the supervision of the inventor. Parts of plants showing mutation were cut from the remainder of the plants by the inventor and planted as cuttings. The plants grown from these cuttings were identified by number and selections were made by the inventor in autumn 1991.

The new cultivar evolved from a branch of an irradiated plant having a different red bract color and different bract shape. The plant was grown out and propagated several times by cuttings by the inventor in Hillscheid, Germany in order to eliminate chimeras and to obtain a plant with stable and uniform characteristics.

Horticultural examinination initiated in 1992 and continuing thereafter has demonstrated that the combination of characteristics as herein disclosed for Fispic are firmly fixed and are retained through successive generations of asexual reproduction.

The following traits have been repeatedly observed and are determined to be basic characteristics of Fispic which in combination distinguish this Poinsettia as a new and distinct cultivar:

1. Light red bract color.
2. Shape of bracts is comparatively narrow and a little pointed.
3. Low and compact plant habit.
4. Medium green foliage.
5. No heat delay and no tendency to develop a bluish tint, making Fispic well suited for early culture under high temperatures.

Fispic has not been observed under all possible environmental conditions. The phenotype may vary significantly with variations in environment such as temperature, light intensity, and daylength without, however, any variance in genotype. The following observations, measurements and comparisons describe plant grown in Hillscheid, Germany, under greenhouse conditions which approximate those generally used in commercial practice.

Of the many commercial cultivars known to the inventor, the most similar in comparison to Fispic is the parent cultivar Peterstar. In general comparison to Peterstar, Fispic has a somewhat lighter red bract color, bracts which are smaller and have a more pointed shape, a lower and more compact plant habit, and more narrow elliptical leaves which are more rugose and strongly lobed than the weakly lobed leaves of Peterstar. In addition, the margins of the leaves of Fispic are undulated and irregularly crenated, and there are fewer cyathia in the cluster due to the more compact habit of Fispic.

When compared to Angelika, the parent of Peterstar and disclosed in U.S. Plant Pat. No. 5,492, Fispic has a lighter red bract color which is more uniform and which does not tend to develop a bluish cast or to fade under less than optimum conditions. Angelika is a strong grower, develops fertile stamens (unlike Fispic), and has generally flat bracts.

When compared to Fisbon, disclosed in a pending applications, Fispic has a more compact growth habit, its bracts and leaves are narrower with longer acuminated tips and a greater degree of rugosity and lobing. The foliage of Fispic is also a darker green.

The accompanying color photographic drawing shows typical inflorescence and foliage of Fispic, with colors being as true as possible with illustratons of this type. In the photograph, a typical mature potted plant of Fispic appears on the left and a mature potted plant of parent cultivar Peterstar appears on the right.

In the following description, color references are made to The Royal Horticultural Society Colour Chart. The color values were determined indoors in a north light. The plants described were grown in Hillscheid, Germany (latitude 50° N.). They were planted as rooted cuttings into 14 cm pots in early August, potted in late-August and pinched 10 days later. Plants were lighted (long day conditions) from mid- September. From October 1, the plants were grown in a greenhouse under natural light conditions at 18° C. night temperature and 18° to 24° C. day temperature. Observations and measurements were taken at the beginning of flowering when three (3) cyathias were open.

Classification:

*Botanical.—Euphorbia pulcherrima.*

*Commercial.*—Poinsettia, cv. Fispic.

Parentage: Induced mutation of Peterstar.

Plant description:

*Form.*—Compact and bushy, 9–11 branches.

*Growth habit.*—Low to medium heights: 25–30 cm.

*Rooting.*—Fast, less than 20 days.

*Blooming season.*—From late November (about 9 weeks of response time).

*Blooming habit.*—Saleable from late November, when 3–6 bracts are fully colored.

*Foliage.*—Size: Leaf is approximately 13–14 cm in length; petiole is 6.5 cm in length. Internodes: 5–15 mm. Color: New foliage: Upper surface, between 143A and 144A; under surface 144A. Old foliage: Upper surface, green 147A; under surface 137C. Leaf petiole: Light red to dark red; base of midrib is light red. Shape: Narrow elliptical shape, with long acuminated tips, rounded base, slightly undulated margins, small pointed lobes, and irregular crenation. Texture: Weak to medium rugosity; lower side, weak veins. Edge of margin: Mainly entire; the middle parts of the leaves often have notches or irregular crenation. Disease resistance: Neither higher tolerance nor higher susceptibility to diseases or pests have been noted.

Flowering description:

*Cyathias.*—Borne: In a narrow cluster. Quantity: 15–19. Retention: Good. Color: Light green, upper part dark red.

*Bracts.*—Elliptical in shape with pointed tips and weak lobes bracts fold along the midrib; lamina is comparatively strongly rugose largest colored bract with petiole is 17.5 cm long; petioles and basal part of midrib are dark red (upper surface) while the remaining veins are the same color as the bract lamina.

*Color.*—Upper surface bright red 45B-C; lower surface approximately 45C.

*Aspect.*—Bracts are borne somewhat upright.

Reproductive organs:

*Glands, nectar cups.*—Orange-yellow.

*Stamens.*—Brown, hardly any fertile stamens.

*Pollen.*—No pollen.

*Styles.*—Red, 6-lobed stigma.

*Ovaries.*—Triangular, 3-celled, 3 ovules.

I claim:

1. A new and distinct Poinsettia plant named Fispic, as illustrated and described.

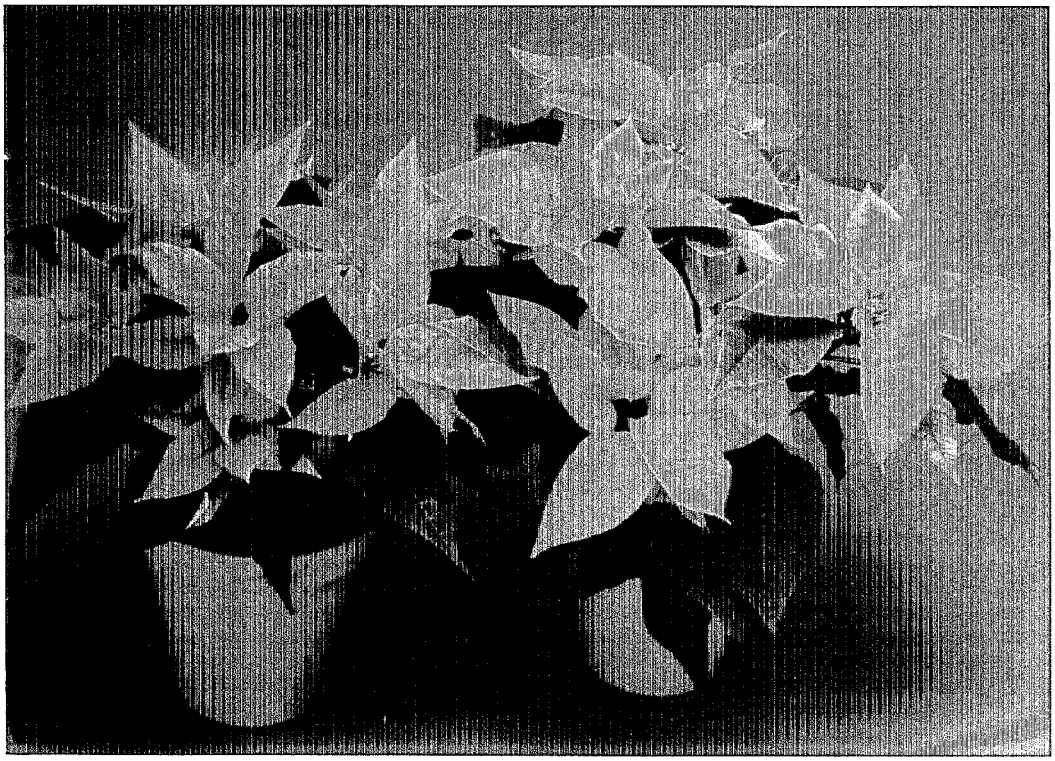

* * * * *